US012429474B2

(12) United States Patent
Urakawa et al.

(10) Patent No.: US 12,429,474 B2
(45) Date of Patent: Sep. 30, 2025

(54) CELL RETAINER

(71) Applicant: SCREEN HOLDINGS CO., LTD., Kyoto (JP)

(72) Inventors: Satoshi Urakawa, Kyoto (JP); Masakazu Sanada, Kyoto (JP)

(73) Assignee: SCREEN HOLDINGS CO., LTD., Kyoto (JP)

(*) Notice: Subject to any disclaimer, the term of this patent is extended or adjusted under 35 U.S.C. 154(b) by 1223 days.

(21) Appl. No.: 17/191,088

(22) Filed: Mar. 3, 2021

(65) Prior Publication Data

US 2021/0293777 A1 Sep. 23, 2021

(30) Foreign Application Priority Data

Mar. 23, 2020 (JP) ................. 2020-051311

(51) Int. Cl.
G01N 33/487 (2006.01)
C12M 1/34 (2006.01)
C12Q 1/02 (2006.01)

(52) U.S. Cl.
CPC ......... *G01N 33/48728* (2013.01); *C12Q 1/02* (2013.01)

(58) Field of Classification Search
None
See application file for complete search history.

(56) References Cited

U.S. PATENT DOCUMENTS

| 4,769,122 A | 9/1988 | Marrese et al. |
| 6,682,649 B1* | 1/2004 | Petersen .......... G01N 33/48728 |
| | | 204/403.01 |
| 2002/0113607 A1 | 8/2002 | Yukimasa |

(Continued)

FOREIGN PATENT DOCUMENTS

| CN | 1377464 A | 10/2002 |
| CN | 1476536 A | 2/2004 |

(Continued)

OTHER PUBLICATIONS

Office Action and Search Report received in corresponding Chinese Patent Application No. 202110218887.1, dated Sep. 22, 2023.

(Continued)

*Primary Examiner* — Holly Kipouros
(74) *Attorney, Agent, or Firm* — Rimon P.C.

(57) ABSTRACT

A cell retainer has a measuring surface that includes a work region in which a plurality of working electrodes are arranged, a reference electrode arranged outward of the work region, a plurality of first regions provided between the work region and the reference electrode, and a second region arranged between each two of the first regions, the two being adjacent to each other in a radial direction. A contact angle in the first region is greater than a contact angle in the work region and a contact angle in the second region. Thus, any of the first regions arranged outward of the work region or the second region serves to restrict the spread of a cell suspension. Moreover, the first regions arranged in multiple tiers enable selection of a drop region and a drop area from a plurality of drop regions and a plurality of drop areas. Accordingly, it is possible to adjust the thickness of a cell layer by selecting the drop area of the cell suspension.

6 Claims, 9 Drawing Sheets

(56) References Cited

U.S. PATENT DOCUMENTS

| | | |
|---|---|---|
| 2003/0194709 A1 | 10/2003 | Yang |
| 2007/0190783 A1 | 8/2007 | Gomez et al. |
| 2010/0261159 A1* | 10/2010 | Hess .................... B01J 19/0046 435/7.1 |
| 2010/0294021 A1 | 11/2010 | Makino et al. |
| 2010/0304423 A1 | 12/2010 | Asai et al. |
| 2014/0038227 A1 | 2/2014 | Aremu |
| 2014/0353171 A1 | 12/2014 | Wilson |
| 2018/0076018 A1 | 3/2018 | Otsuji |
| 2021/0102911 A1 | 4/2021 | Saito |
| 2022/0244210 A1* | 8/2022 | Urakawa .............. G01N 27/227 |

FOREIGN PATENT DOCUMENTS

| | | |
|---|---|---|
| CN | 103482885 A | 1/2014 |
| CN | 107818912 A | 3/2018 |
| CN | 110662843 A | 1/2020 |
| JP | H11-304666 A | 11/1999 |
| JP | 2001-279175 A | 10/2001 |
| JP | 2002-031617 A | 1/2002 |
| JP | 2002-523726 A | 7/2002 |
| JP | 2003-78171 A | 3/2003 |
| JP | 2005-522219 A | 7/2005 |
| JP | 2007-292730 A | 11/2007 |
| JP | 2008-41277 A | 2/2008 |
| JP | 2008-258296 A | 10/2008 |
| JP | 2010-022227 A | 2/2010 |
| JP | 2012-47610 A | 3/2012 |
| JP | 2014-116417 A | 6/2014 |
| JP | 2015-508997 A | 3/2015 |
| JP | 2019-110794 A | 7/2019 |
| JP | 2020-14308 A | 1/2020 |
| KR | 2018-0041628 A | 4/2018 |
| WO | 99/34202 A1 | 7/1999 |
| WO | 01/25769 A2 | 4/2001 |
| WO | 02/29402 A2 | 4/2002 |

OTHER PUBLICATIONS

Office Action dated on Jun. 27, 2024 issued in the corresponding Chinese Patent Application No. 202110218887.1, w/ English Translation.

Jing-xian Zhang, et al., "Study of Preparation and Dynamic Hydrophobicity of Superhydrophobic Surfaces With Micro-Nano Textures" Applied Mathematics and Mechanics vol. 35, No. 3, Mar. 15, 2014, w/ English abstract.

Wan, Yanling & Yang, Jian & Yu, Huadong, "Superhydrophobic Surface Prepared by Micro-milling and WEDM on Aluminum Alloy," Materials Research Express. Jun. 6, 2018.

Office Action dated on Mar. 6, 2024 issued in the corresponding Chinese Patent Application No. 202110218887.1, w/ English Translation.

"Synthesis, Properties and Applications of Janus Nanoparticles", Chinese Master's Theses Full-text Database, Engineering Science and Technology I, Feb. 2015, B020-424, w/ partial translation.

* cited by examiner

IN THE CASE OF CONTROL IN INNER FIRST REGION

IN THE CASE OF CONTROL IN INTERMEDIATE FIRST REGION

IN THE CASE OF CONTROL IN OUTER FIRST REGION

CELL RETAINER

RELATED APPLICATIONS

This application claims the benefit of Japanese Application No. 2020-051311, filed on Mar. 23, 2020, the disclosure of which is incorporated by reference herein.

BACKGROUND OF THE INVENTION

Field of the Invention

The present invention relates to a cell retainer.

Description of the Background Art

In order to measure induced electricity generated by tissues or cells such as nerve cells, a system is conventionally known in which the extracellular potential is measured using an MEA electrode called a micro-electrode array, which is a cell retainer having a plurality of electrodes provided on its bottom surface. For example, such an MEA electrode is described in Japanese Unexamined Patent Application (Published Japanese translation of a PCT Application) No. 2002-523726.

The MEA electrode includes a plurality of working electrodes and a reference electrode provided on a measuring surface. In the measurement of the extracellular potential, firstly, a liquid (cell suspension) such as a culture solution containing cells or tissue sections is dropped on the working electrodes. After a while, the cells or the tissue sections in the liquid settle down on the working electrodes, forming a cell layer. After the formation of the cell layer, the extracellular potential of the cell layer is measured.

SUMMARY OF THE INVENTION

In the case of measuring the extracellular potential of the cell layer, the reference electrode needs to be not in contact with the cell layer. Thus, it becomes necessary to prevent the cell suspension when being dropped from coming in contact with the reference electrode. That is, it is necessary to prevent a region over which the cell suspension is dropped from extending to the reference electrode.

If the concentration of the cell suspension and the amount of drop of the cell suspension are constant, the thickness of the cell layer is dependent on the area of the region over which the cell suspension is dropped (i.e., a drop area). The larger the drop area of the cell suspension, the smaller the thickness of the cell layer. The smaller the drop area of the cell suspension, the greater the thickness of the cell layer.

It is an object of the present invention to provide a technique that enables adjusting the region over which the cell suspension is dropped, and the drop area.

One aspect of the present invention is a cell retainer having a measuring surface on which a cell suspension is dropped. The measuring surface includes a work region in which a plurality of working electrodes are arranged, a reference electrode arranged outward of the work region, a plurality of first regions provided between the work region and the reference electrode, and a second region arranged between each two of the plurality of first regions, the two being adjacent to each other in a radial direction. A contact angle in the plurality of first regions is greater than a contact angle in the work region and a contact angle in the second region.

Any one of the first regions that is arranged outward of the work region or the second region serves to restrict the spread of the cell suspension. Accordingly, the region over which the cell suspension is dropped can be adjusted to the inside of the first region. Moreover, the first regions arranged in the plurality of tiers enable selection of a drop region and a drop area from a plurality of drop regions and a plurality of drop areas. Accordingly, it is possible to adjust the thickness of the cell layer by selecting the drop area of the cell suspension.

Preferably, the first regions each may surround the work region in a ring.

The first regions having a ring shape serve to restrict the spread of the cell suspension all the way in the circumferential direction. Accordingly, it is possible to more precisely adjust the drop region.

Preferably, the first regions each may have a circular ring shape.

This makes the spread of the cell suspension isotropic. Accordingly, the thickness of the cell layer also becomes isotropic.

Preferably, the contact angle in the plurality of first regions may be greater by 40° or more than the contact angle in the work region and the contact angle in the second regions.

This efficiently restricts the spread of the cell suspension at the inner edges of the first regions.

Preferably, the plurality of first regions may be planar in shape, and a contact angle with a planar surface of a material for the plurality of first regions may be greater than the contact angle in the work region and the contact angle in the second region.

The contact angle is set by selection of the material.

Preferably, surfaces of the plurality of first regions may have asperities in at least a radial direction, and a material for the plurality of first regions may have a greater contact angle with a surface having asperities than with a planar surface.

Even if the contact angle with the plane surface of the material for the first regions is not sufficiently greater than the contact angle in the work region and the contact angle in the second region, the presence of asperities results in a sufficient increase in the contact angle in the first regions.

These and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
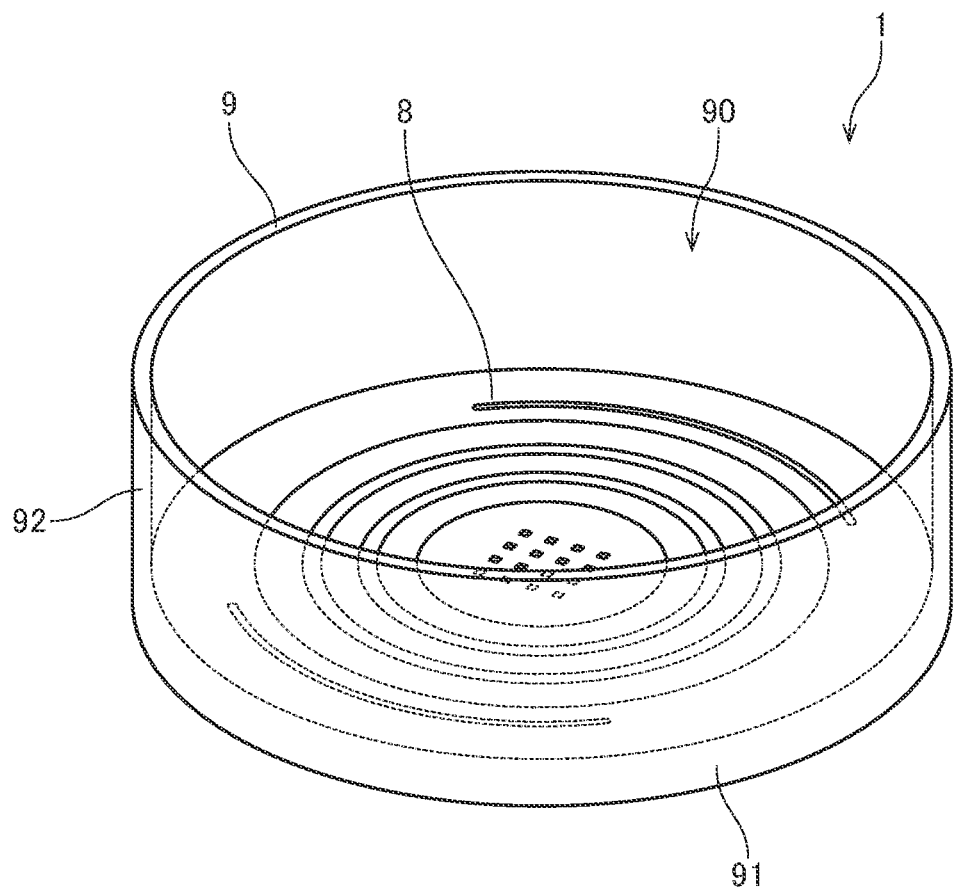
FIG. 1 is a perspective view of a cell retainer according to a first embodiment.

Embodiments of the present invention will be described hereinafter with reference to the drawings. In the following description, a direction parallel to the bottom surface of a cell retainer is referred to as a "horizontal direction," and a direction orthogonal to the horizontal direction is referred to as an "up-down direction." It is, however, noted that the cell retainer during use does not necessarily have to be in such a posture that the cell retainer has a horizontal bottom surface. A direction along the arc of a circle centered on the central portion of a measuring region is referred to as a "circumferential direction," and a direction extending from the central portion of the measuring region is referred to as a "radial direction."

Note that the drawings are drawn in schematic form, and part of the configuration in the drawings may be expressed in an exaggerated way for the sake of convenience of description. That is, the mutual relationship between the size and position of the configuration illustrated in the drawings is not always accurate and may be appropriately changed.

1. First Embodiment

1-1. Configuration of Cell Retainer

Figure 2:
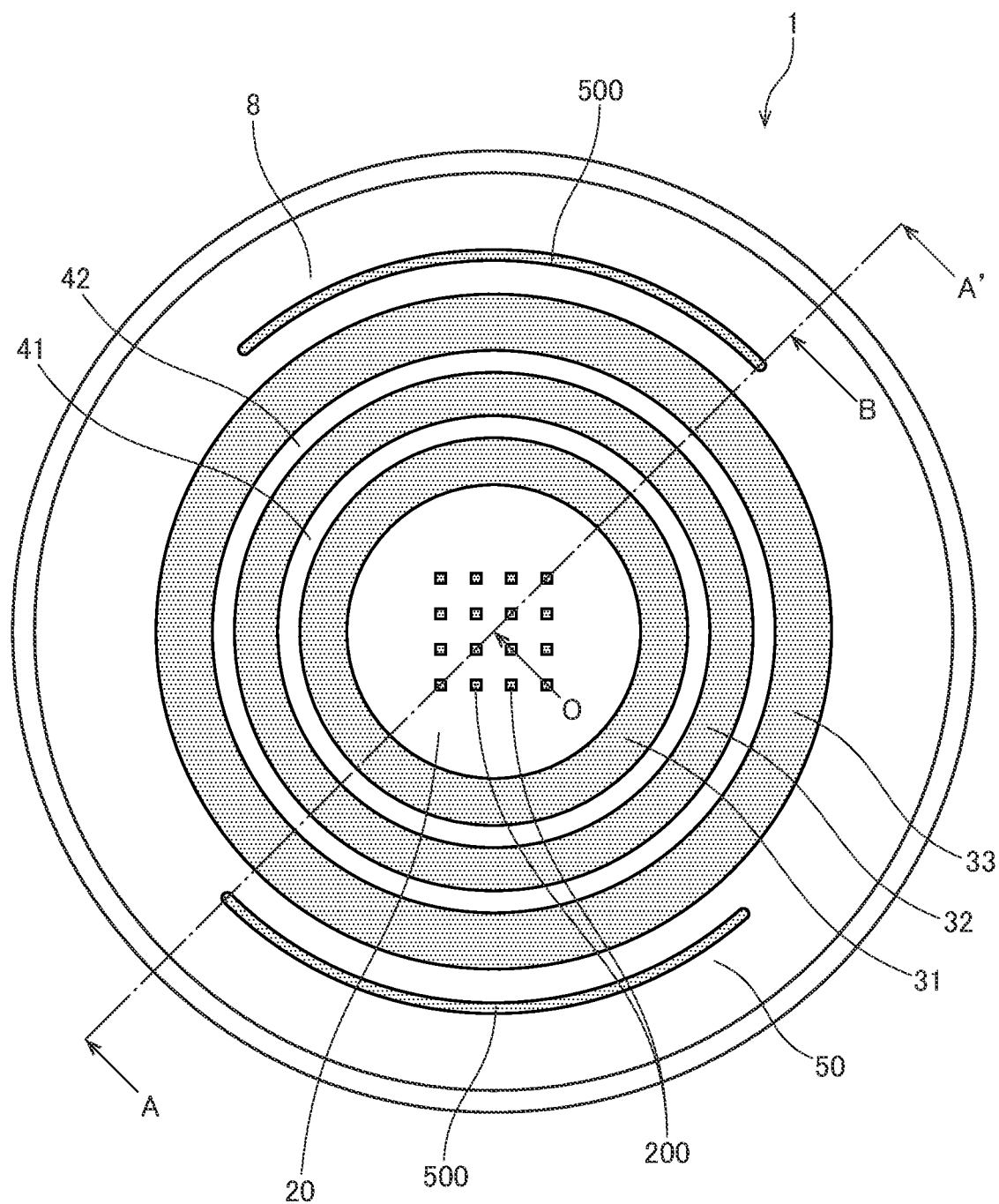
FIG. 2 is a top view of the cell retainer according to the first embodiment.

A cell retainer 1 according to a first embodiment of the present invention will be described with reference to FIGS. 1 and 2. FIG. 1 is a perspective view of the cell retainer 1. FIG. 2 is a top view of the cell retainer 1. In FIG. 2, some regions are illustrated in color in order to clarify the boundaries of these regions. Wiring that extends from working electrodes 200 and reference electrodes 500 described later is not illustrated in FIGS. 1 and 2.

The cell retainer 1 is a container that houses and holds therein a cell layer and a culture medium and that is used to measure electrical characteristics of the held cell layer. The cell retainer 1 has electrodes formed on its bottom surface in order to measure electrical characteristics of cells or tissues housed in the cell retainer 1. The cell retainer 1 is configured to measure electrical characteristics of a cell layer that is formed by dropping a liquid (cell suspension) such as a culture solution containing cells or tissue sections. Alternatively, the cell retainer 1 may be used to measure electrical characteristics of biomedical tissues such as brain slice samples or a cell layer that is formed by incubating cells in the cell retainer 1.

As illustrated in FIGS. 1 and 2, the cell retainer 1 includes a body portion 9 having a cup-shaped recess 90, and a measuring surface 8 that forms the bottom surface of the recess 90. The cell retainer 1 according to the present embodiment is a closed-end cylindrical container with only one recess 90 formed in the body portion 9. Thus, the body portion 9 includes a planar base plate portion 91 and a side wall portion 92 that extends upward from the edge of the base plate portion 91. The upper surface of the base plate portion 91 serves as the measuring surface 8.

The cell retainer 1 according to the present embodiment is a closed-end cylindrical container with only one recess 90 formed in the body portion 9, but the present invention is not limited to this example. The cell container may be a so-called multi-well plate with a plurality of recesses 90 formed in the body portion 9.

When a cell suspension is dropped on the cell retainer 1, for example, the cell retainer 1 is placed on and fixed to a placing base such that the measuring surface 8 faces vertically upward. Then, a cell suspension is dropped with a predetermined capacity on the measuring surface 8. The amount of drop of the cell suspension is, for example, about several microliters (μL) (more specifically, for example, about 4 μL). After the dropping of the cell suspension, the cell retainer 1 stands by for some time while maintaining its posture. The cells or the tissue sections contained in the dropped cell suspension settle down in the liquid, forming a sheet cell layer on the measuring surface 8. In this way, the cell layer is formed in a region over which the cell suspension is spread out (i.e., a drop region). A detailed method for dropping the cell suspension will be described later.

The measuring surface 8 includes a work region 20, an inner first region 31, an intermediate first region 32, an outer first region 33, an inner second region 41, an outer second region 42, and a reference region 50. The measuring surface 8 according to the present embodiment is circular in shape as viewed from above, but the present invention is not limited to this example. The measuring surface may have an oval shape, any regular polygonal shape such as a square, or any other shape such as a rectangle.

The work region 20 is a region provided in the center of the measuring surface 8.

The three first regions 31, 32, and 33 are regions arranged outward of the work region 20. The first regions 31, 32, and 33 each surround the work region 20 in a ring. Specifically, the first regions 31, 32, and 33 are concentrically circular regions.

The inner first region 31, the intermediate first region 32, and the outer first region 33 are arranged at intervals in the radial direction in this order from the radially inward side to the radially outward side.

The two second regions 41 and 42 are regions arranged outward of the work region 20 and the inner first region 31. The second regions 41 and 42 each also surround the work region 20 in a ring. Specifically, the second regions 41 and 42 are concentrically circular regions.

Each of the two second regions 41 and 42 is arranged in the radial direction between each adjacent two of the first regions 31, 32, and 33. Specifically, the inner second region 41 is arranged between the inner first region 31 and the intermediate first region 32. The outer second region 42 is arranged between the intermediate first region 32 and the outer first region 33.

The reference region 50 is a region arranged outward of the outer second region 42.

In this way, the work region 20, the inner first region 31, the inner second region 41, the intermediate first region 32, the outer second region 42, the outer first region 33, and the reference region 50 are arranged adjacent to one another in the radial direction in this order from the radially inward side.

The measuring surface 8 also includes a plurality of working electrodes 200 and two reference electrodes 500 arranged thereon.

The working electrodes 200 are all arranged within the work region 20. The working electrodes 200 are aligned two-dimensionally within the work region 20 as viewed from above. In the present embodiment, 16 working electrodes 200 are arranged in a matrix of four rows and four columns, but the number and arrangement of working electrodes 200 are not limited to this example. The working electrodes 200 may be arranged at intervals from one another.

The working electrodes 200 according to the present embodiment are all square in shape as viewed from above, but the working electrodes 200 may have a circular shape, a rectangular shape, or any other arbitrary shape.

The reference electrodes 500 are both arranged in the reference region 50. The reference electrodes 500 according to the present embodiment extend in the shape of an arc along the outer edge portion of the outer first region 33. Note that the number of reference electrodes 500 is not limited to two, and may be one or three or more. The shape of the reference electrodes 500 is also not limited to the arc shape. Like the working electrodes 200, the reference electrodes 500 may have a square shape, a rectangular shape, or any other arbitrary shape as viewed from above.

Specifically, in the present embodiment, the surface of the work region 20 is formed of $SiO_x$ film, except the portions corresponding to the working electrodes 200. The surfaces of the first regions 31, 32, and 33 are made of gold (Au). The surfaces of the second regions 41 and 42 are formed of $SiO_x$ film. The surfaces of the reference regions 50 are formed of $SiO_x$ film, except the portions corresponding to the reference electrodes 500. The working electrodes 200 and the reference electrodes 500 are made of gold (Au). In the present embodiment, the surfaces of the work region 20, the first regions 31, 32, and 33, and the second regions 41 and 42 are each obtained by forming a material for each region in planar form.

A contact angle with the plane surface of the $SiO_x$ film is less than 30°, and a contact angle with the plane surface of gold (Au) is approximately 80°. Thus, contact angles in the work region 20 and the second regions 41 and 42 are less than 30°, and a contact angle in the first regions 31, 32, and 33 is approximately 80°.

In this way, the contact angle in the first regions 31, 32, and 33 is greater than the contact angle in the work region 20 and the contact angle in the second regions 41 and 42. The "contact angle in the work region 20" as used herein refers to the "contact angle with the portion of the work region 20, excluding the working electrodes 200." Accordingly, it is possible to restrict the entry of the liquid dropped on the work region 20 and the second regions 41 and 42 into the first regions 31, 32, and 33 at the boundaries between each of the first regions 31, 32, and 33 and each of the work region 20 and the second regions 41 and 42.

More specifically, as described above, the contact angle in the first regions 31, 32, and 33 is greater by 40° or more than the contact angle in the work region 20 and the contact angle in the second regions 41 and 42. Accordingly, it is possible to more efficiently restrict the entry of the liquid dropped on the work region 20 and the second regions 41 and 42 into the first regions 31, 32, and 33 at the boundaries between each of the first regions 31, 32, and 33 and each of the work region 20 and the second regions 41 and 42.

In the present embodiment, the first regions 31, 32, and 33 are planar in shape as described above. Then, the contact angle with the planar surface of the material (gold (Au)) for the first regions 31, 32, and 33 is greater than the contact angles in the work region 20 and the second regions 41 and 42. That is, it is possible to restrict the entry of the liquid dropped on the work region 20 and the second regions 41 and 42 into the first regions 31, 32, and 33 without complicating the surface shape of the first regions 31, 32, and 33.

1-2. How Cell Suspension Spreads

In the case of measuring the cell layer formed from the cell suspension in the cell retainer 1, firstly, a liquid (cell suspension) such as a culture solution containing cells or tissue sections is dropped on the working electrodes. After a while, the cells or the tissue sections in the liquid settle down on the working electrodes, forming a cell layer. After the formation of the cell layer, the extracellular potential of the cell layer is measured.

Figure 3:
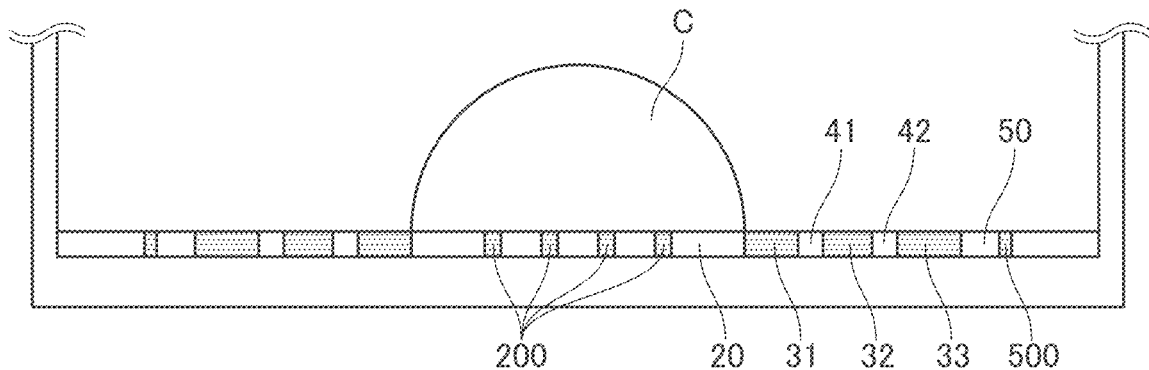
FIG. 3 is a diagram schematically illustrating states of the cell retainer according to the first embodiment after a cell suspension is dropped.
Figure 3:
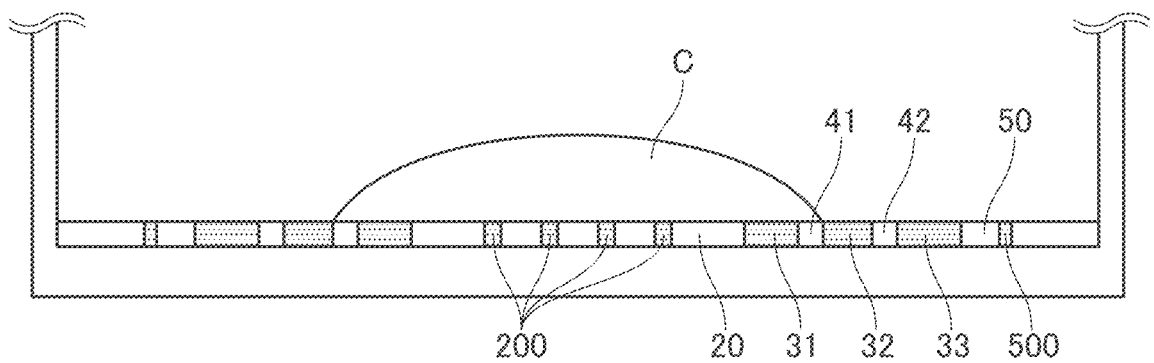
Figure 3:
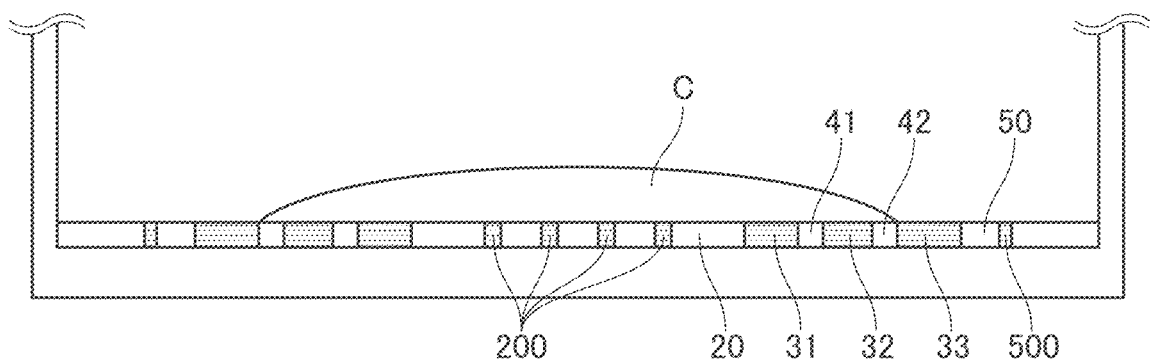

Here, how the dropped cell suspension spreads will be described with reference to FIG. 3. FIG. 3 is a diagram schematically illustrating states after the cell suspension is dropped. In FIG. 3, a portion of the measuring surface 8 in section A-A' is illustrated not in the actual sectional shape but in the shape of blocks colored in the same manner as in FIG. 2 in order to discern colored portions in FIG. 2. That is, in FIG. 3, colored portions and non-colored portions in FIG. 2 are divided into blocks for convenience's sake and illustrated as a section. Although repeatedly expressed, the sectional view divided into blocks in FIG. 3 is different from the actual sectional shape of the cell retainer 1.

When the cell suspension is dropped on the central portion of the work region 20 using a micropipette or other instruments, the cell suspension easily spreads out into the work region 20 because the contact angle in the work region 20 is relatively small. Thus, the cell suspension spreads to the outer edge portion of the work region 20.

As described above, the contact angle with the surface of the inner first region 31 is greater than the contact angle in the work region 20. This difference in contact angle inhibits the entry of the cell suspension from the outer edge portion of the work region 20 into the inner first region 31. Accordingly, the spread of the cell suspension is stopped at the inner edge portion of the inner first region 31. That is, it is possible to perform control such that the range of drop of the cell suspension falls within the inner first region 31. In this case, the cell suspension has a sectional shape C as in the case where the range of drop of the cell suspension is controlled in the inner first region" illustrated in the upper section of FIG. 3.

Next, in the case of a desire to expand the range of drop of the cell suspension, for example, the cell suspension is dropped while being spread out to cover the whole of the inner first region 31. In this case, the cell suspension dropped on the inner first region 31 flows from the inside of the inner first region 31 into the work region 20 and the inner second region 41, both of which are adjacent to the inner first region 31 and have smaller contact angles than the inner first region 31. Thereafter, the cell suspension spreads to the insides of the work region 20 and the inner second region 41, both having relatively small contact angles. Accordingly, the cell suspension spreads to cover the whole of the work region 20, the inner first region 31, and the inner second region 41.

In the vicinity of the outer edge portion of the inner second region 41, the contact angle with the surface of the adjacent intermediate first region 32 is greater than the contact angle with the surface of the inner second region 41. This difference in contact angle inhibits the entry of the cell suspension from the outer edge portion of the inner second region 41 into the intermediate first region 32. Accordingly, the spread of the cell suspension is stopped at the inner edge portion of the intermediate first region 32. That is, it is possible to perform control such that the range of drop of the cell suspension falls within the inside of the intermediate first region 32. In this case, the cell suspension has a sectional shape C as in "the case where the range of drop of the cell suspension is controlled in the intermediate first region" illustrated in the middle section of FIG. 3.

Next, in the case of a desire to further expand the range of drop of the cell suspension, for example, the cell suspension is dropped while being spread out to cover the whole of the inner first region 31 and the intermediate first region 32.

In this case, the cell suspension dropped on the inner first region 31 flows from the inside of the inner first region 31 into the work region 20 and the inner second region 41, both of which are adjacent to the inner first region 31 and have smaller contact angles than the inner first region 31. The cell suspension dropped on the intermediate first region 32 flows from the inside of the intermediate first region 32 into the inner second region 41 and the outer second region 42, both of which are adjacent to the intermediate first region 32 and have smaller contact angles than the intermediate first region 32.

Thereafter, the cell suspension spreads to the insides of the work region 20, the inner second region 41, and the outer second region 42 that have relatively small contact angles. Accordingly, the cell suspension spreads to cover the whole of the work region 20, the inner first region 31, the inner second region 41, the intermediate first region 32, and the outer second region 42.

In the vicinity of the outer edge portion of the outer second region 42, the contact angle with the surface of the adjacent outer first region 33 is greater than the contact angle with the surface of the outer second region 42. This difference in contact angle inhibits the entry of the cell suspension from the outer edge portion of the outer second region 42 into the outer first region 33. Accordingly, the spread of the cell suspension is stopped at the inner edge portion of the outer first region 33. That is, it is possible to perform control such that the range of drop of the cell suspension falls within the outer first region 33. In this case, the cell suspension has a sectional shape C as "in the case where the range of drop of the cell suspension is controlled in the outer first region" illustrated in the lower section of FIG. 3.

In this way, since the contact angle in the first regions 31, 32, and 33 is greater than the contact angle in the work region 20 and the contact angle in the second regions 41 and 42, any one of the first regions 31, 32, and 33 that is located adjacent to and outward of the work region 20 or the second region 41 or 42 serves to restrict the spread of the cell suspension. Accordingly, the drop region of the cell suspension can be adjusted to the inside of the first region 31, 32, or 33

Besides, the first regions 31, 32, and 33 arranged in multiple tiers enable selection of the drop area of the cell suspension from a plurality of areas. In the present embodiment, the drop area of the cell suspension can be selected from one of the following: the area of a region located inward of the inner first region 31, the area of a region located inward of the intermediate first region 32, and the area of a region located inward of the outer first region 33.

Accordingly, it is possible to select the drop region of the cell suspension and the drop area thereof and to adjust the thickness of the cell layer that is to be formed thereafter.

In the present embodiment, the first regions 31, 32, and 33 each surround the work region 20 in a ring. In this way, the first regions 31, 32, and 33, each having a ring shape, serve to restrict the spread of the cell suspension all the way in the circumferential direction. Accordingly, it is possible to more precisely adjust the drop region of the cell suspension. As will be described later, the first regions 31, 32, and 33 have gaps of slight widths in the circumferential direction. However, the first regions 31, 32, and 33 all have a ring shape, excluding these gaps, and therefore, still have enough effect to restrict the spread of the cell suspension.

In the present embodiment, the first regions 31, 32, and 33 each have a circular ring shape. This makes the spread of the cell suspension isotropic in the region located inward of each of the first regions 31, 32, and 33. Accordingly, the thickness of the cell layer, which is formed after the cell suspension is dropped, also becomes isotropic.

Figure 4:
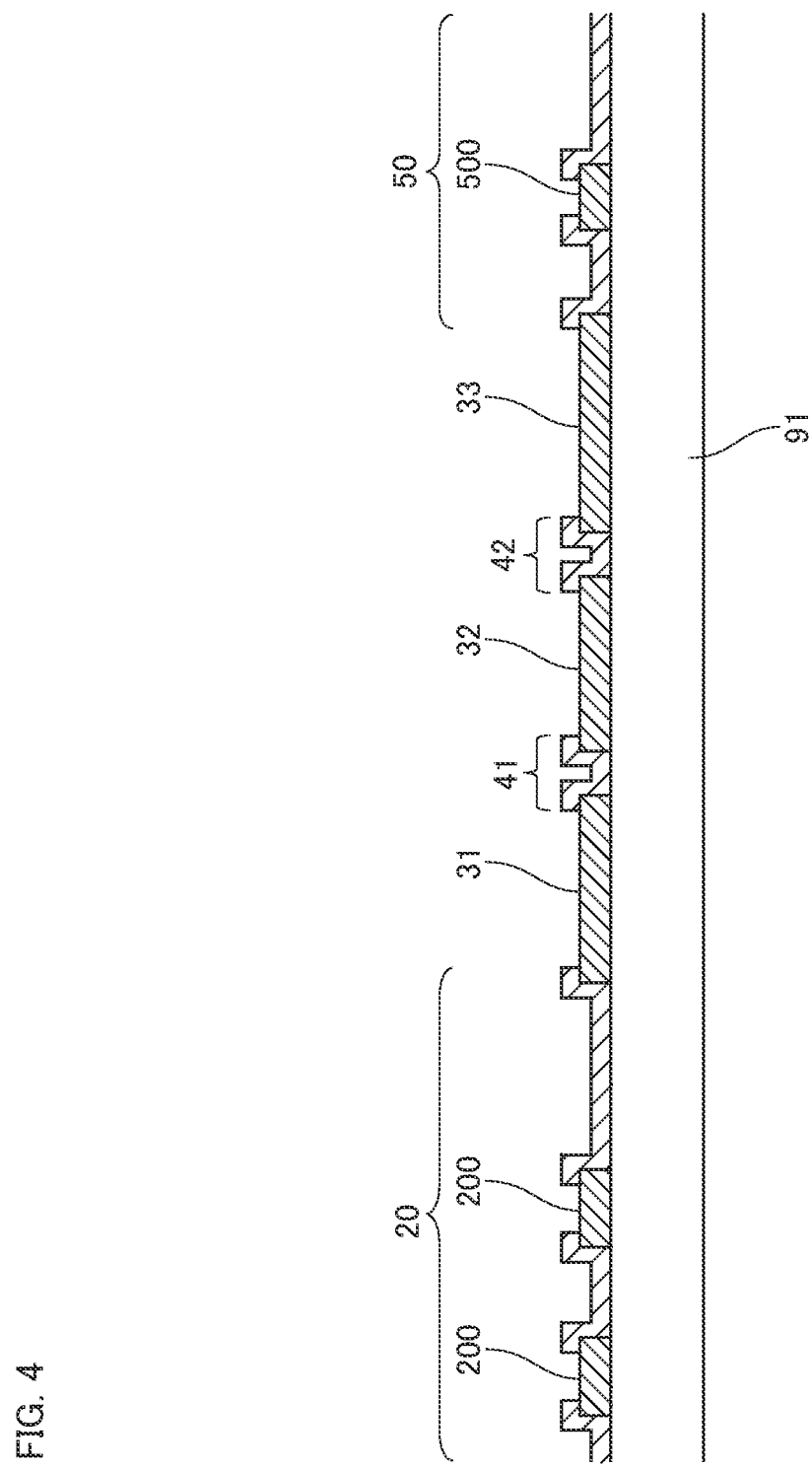
FIG. 4 is a partial sectional view of the cell retainer according to the first embodiment.

1-3. Sectional Shape of Measuring Surface Next, a sectional shape of the measuring surface 8 according to the present embodiment will be described with reference to FIG. 4. FIG. 4 is a sectional view of a section O-B of the cell retainer 1.

In the formation of the measuring surface 8, firstly, a region of the measuring surface 8 that is made of gold (Au) is formed on the upper face of the base plate portion 91 of the body portion 9. For example, a metal film made of gold (Au) (hereinafter, referred to as an "Au metal film") is formed on the upper face of the base plate portion 91 of the body portion 9 by liquid phase deposition or vapor phase deposition. Thereafter, the working electrodes 200, the reference electrodes 500, wiring (e.g., wiring 201 illustrated in FIG. 5) that extends from the working electrodes 200 and the reference electrodes 500, and the first regions 31, 32, and 33 are formed by lithography through the formation and etching of a resist pattern and the removal of the resist pattern. Note that these regions made of gold (Au) may be formed by a lift-off method.

Next, a region made of $SiO_x$ is formed. For example, a layer of $SiO_x$ insulator film is formed on the base plate portion 91 and the Au metal film by vacuum deposition or sputtering. Thereafter, the formation and etching of a resist pattern and the removal of a resist are performed by lithography to expose the working electrodes 200, the reference electrodes 500, and the first regions 31, 32, and 33. As a result, portions where the $SiO_x$ insulator film remains become the work region 20, the second regions 41 and 42, and the reference region 50. Note that the $SiO_x$ insulator film on the wiring is not removed.

Here, the $SiO_x$ insulator film slightly remains on the Au metal film in the edge portions of the regions of Au metal film including the working electrodes 200, the reference electrodes 500, and the first regions 31, 32, and 33. Accordingly, the Au metal film and the $SiO_x$ insulator film that form the measuring surface 8 take the sectional shape as illustrated in FIG. 4. By way of example, the inner edge portion of the $SiO_x$ insulator film that forms the inner second region 41 is laminated on the outer edge portion of the Au metal film that forms the inner first region 31.

Figure 5:
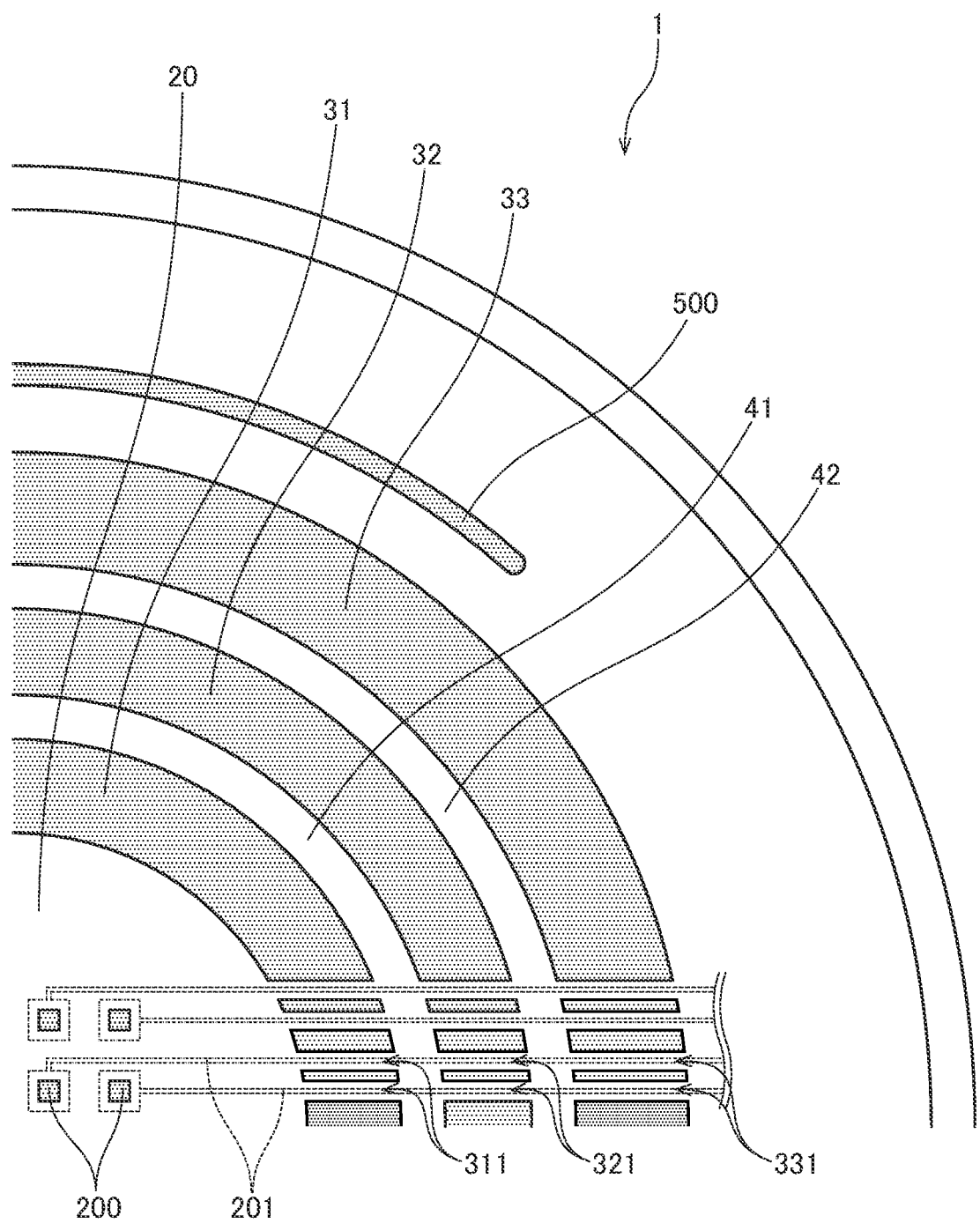
FIG. 5 is a partial top view of the cell retainer according to the first embodiment.

Here, a case will be described with reference to FIG. 5, in which the wiring extending from the working electrodes 200 is formed together with the working electrodes 200 on the upper surface of the base plate portion 91. FIG. 5 is a partial top view of the cell retainer 1. In the present embodiment, the first regions 31, 32, and 33, the working electrodes 200, the reference electrodes 500, wiring 201 that extends from the working electrodes 200, and wiring (not shown) that extends from the reference electrodes 500 are formed of the same material as the same layer.

In such a case, the wiring 201 extending from the working electrodes 200 may be arranged crossing over the first regions 31, 32, and 33. In that case, the first regions 31, 32, and 33 need to be arranged not overlapping the wiring 201 and peripheral portions of the wiring 201 in order to prevent continuity between the first regions 31, 32, and 33 and the wiring 201. For this reason, for example, the first regions 31, 32, and 33 respectively have breaks 311, 321, and 331 in the circumferential direction for installation of the wiring 201 as illustrated in FIG. 5. Note that these breaks 311, 321, and 331 have only slight widths in the circumferential direction, and therefore, the first regions 31, 32, and 33 still have enough effect to restrict the spread of the cell suspension.

2. Variations

While one embodiment of the present invention will be described thus far, the present invention is not intended to be limited to the embodiment described above.

Figure 6:
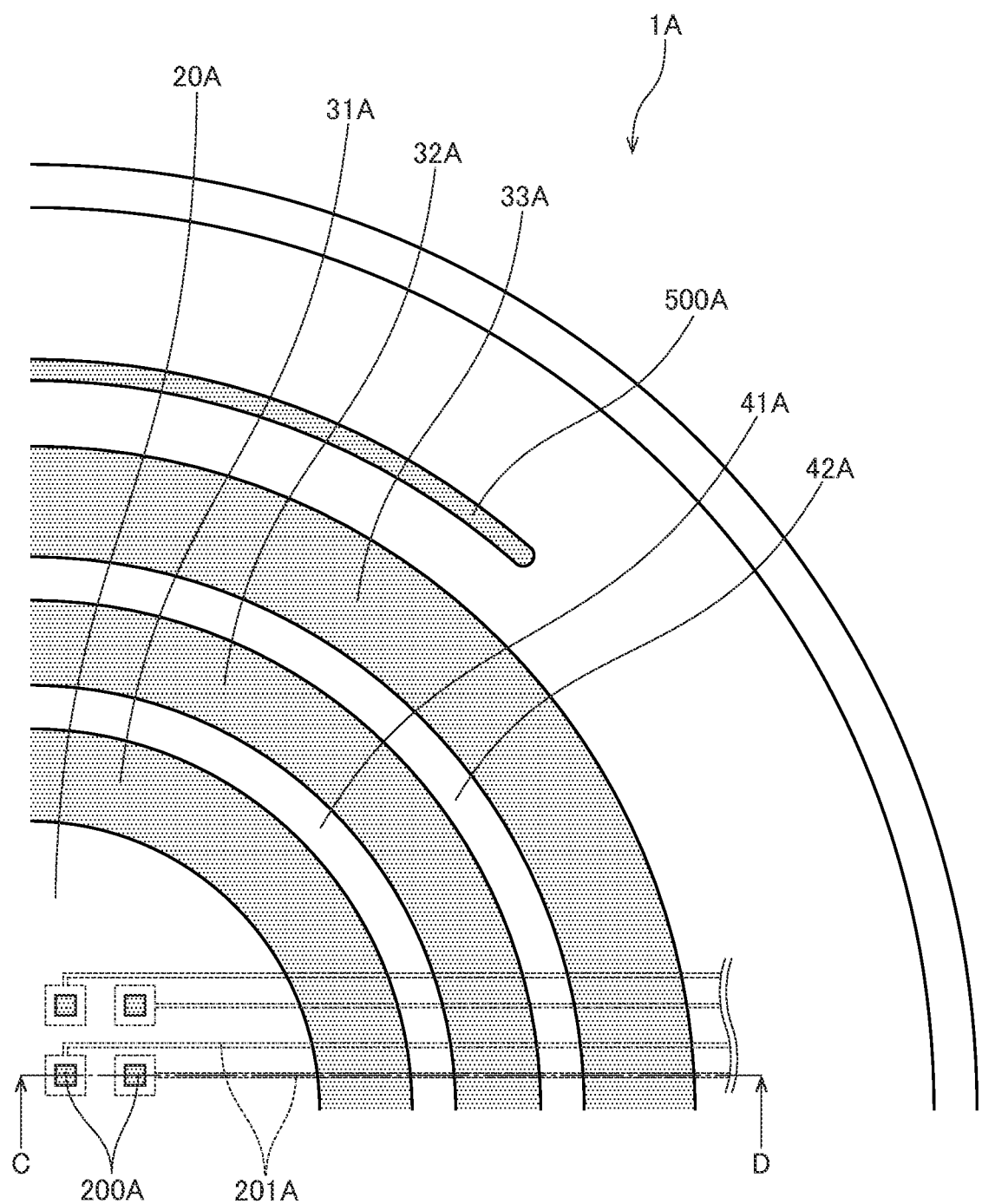
FIG. 6 is a partial top view of a cell retainer according to a variation.
Figure 7:
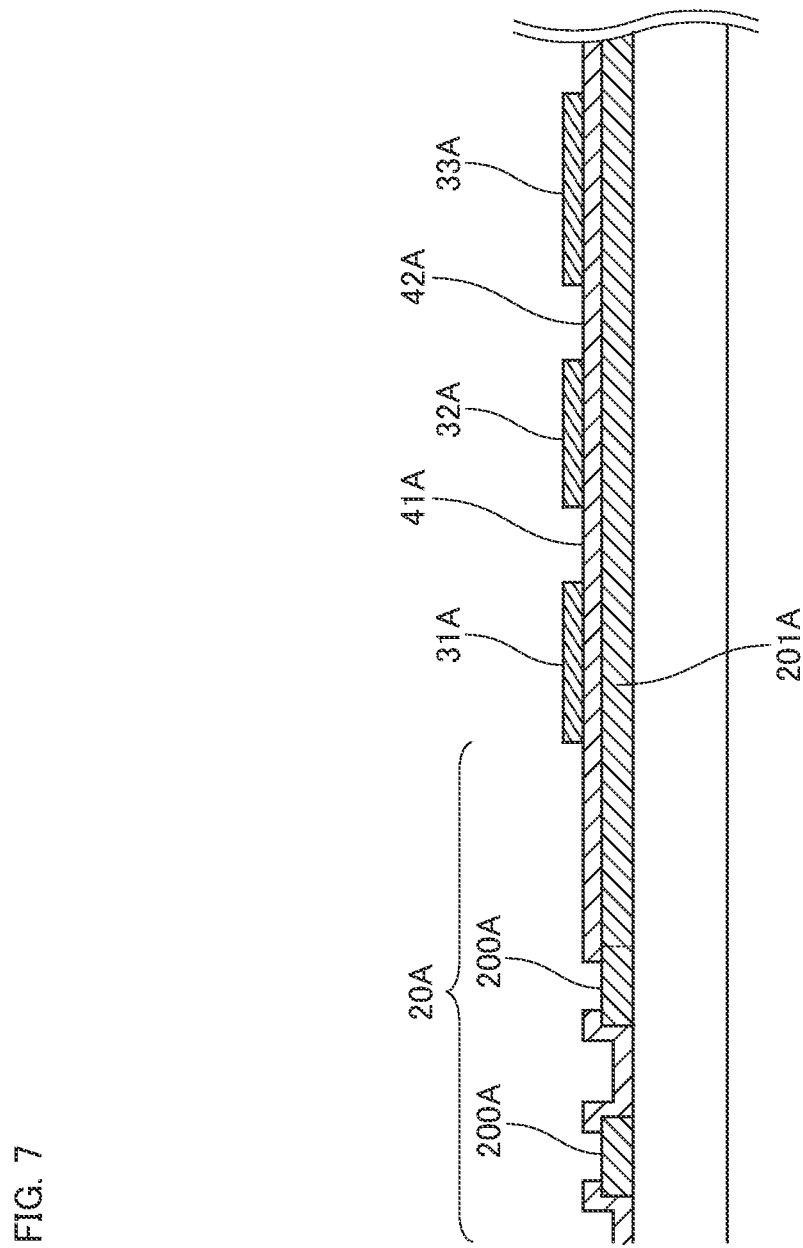
FIG. 7 is a partial sectional view of the cell retainer according to the variation.

FIG. 6 is a partial top view of a cell retainer 1A according to one variation. FIG. 7 is a sectional view of a section C-D of the cell retainer 1A in the example illustrated in FIG. 6. In this cell retainer 1A, wiring 201A that extends from working electrodes 200A and a metal film forming the first regions 31A, 32A, and 33A are arranged overlapping each other in the up-down direction, with a layer of $SiO_x$ insulator film sandwiched therebetween and forming second regions 41A and 42A.

As illustrated in FIG. 6, this configuration eliminates the need to provide the first regions 31A, 32A, and 33A with breaks in the circumferential direction. Accordingly, the first regions 31A, 32A, and 33A have an improved effect of restricting the spread of the cell suspension.

As illustrated in FIG. 7, in this cell retainer 1A, the $SiO_x$ insulator film is formed on the metal layer forming the working electrodes 200A, the wiring 201A, and the reference electrodes 500A. The $SiO_x$ insulator film is formed on the entire measuring surface 8, except the portions corresponding to the working electrodes 200A and the reference electrodes 500A. Accordingly, the work region 20A excluding the working electrodes 200A, the first regions 31A, 32A, and 33A, the second regions 41A and 42A, and the reference region 50A excluding and the reference electrodes 500A are covered with the $SiO_x$ insulator film. Then subsequently, a layer having a greater contact angle than the $SiO_x$ insulator film is formed on the $SiO_x$ insulator film in the first regions 31A, 32A, and 33A. By so doing, it is possible to arrange the first regions 31A, 32A, and 33A and the wiring 201A overlapping each other in the up-down direction.

In the case where the first regions 31A, 32A, and 33A and the wiring 201A are formed as different layers as described above, the first regions 31A, 32A, and 33A and the wiring 201A may be made of different materials. The first regions 31A, 32A, and 33A do not necessarily have to have conductivity and therefore may be formed of a material that has a greater contact angle than the materials for the working region 20A and the second regions 41A and 42A and that is different from the material for the electrodes 200A and 500A and the wiring 201A.

Figure 8:
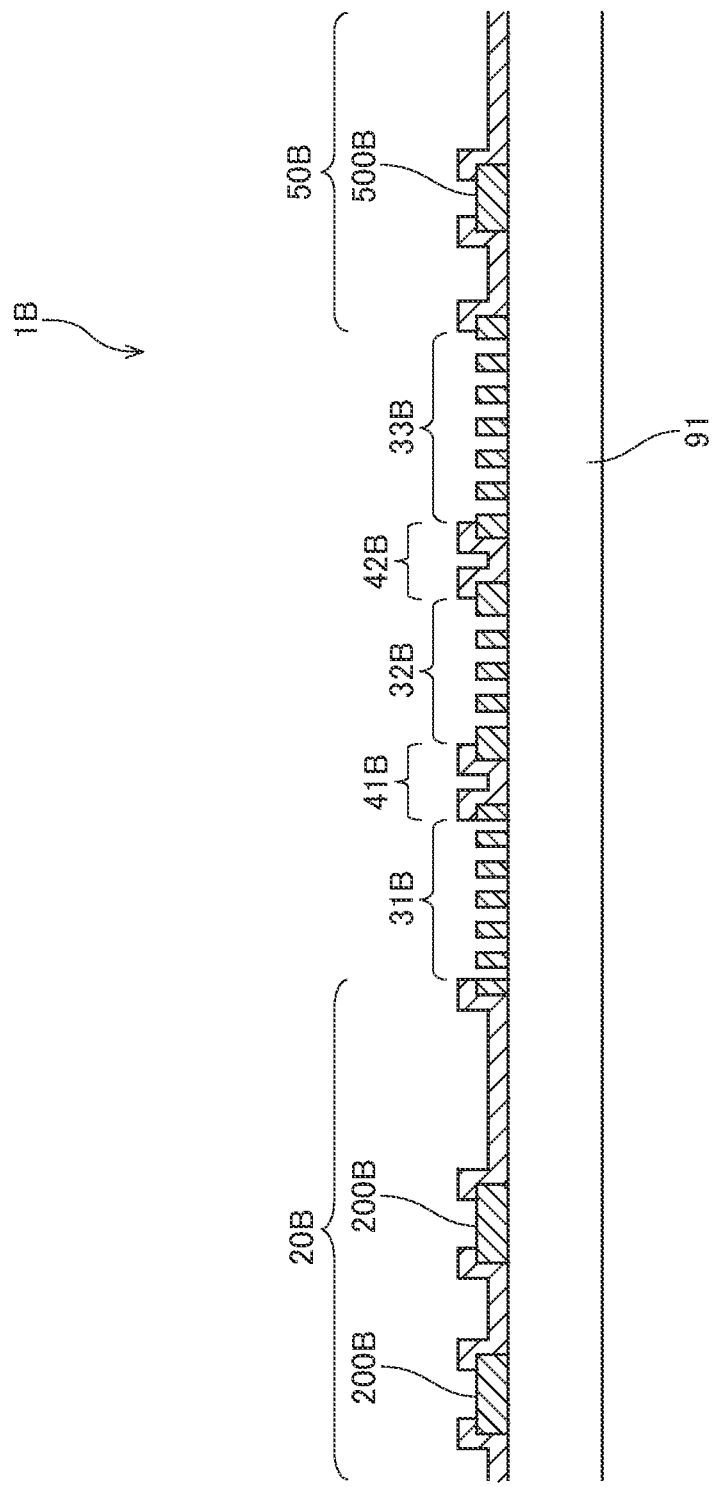
FIG. 8 is a partial sectional view of a cell retainer according to another variation.

FIG. 8 is a partial sectional view of a cell retainer 1B according to another variation. This cell retainer 1B differ from the cell retainer 1 according to the first embodiment in that its first regions 31B, 32B, and 33B are made of different materials and have different shapes.

In this cell retainer 1B, a work region 20B, second regions 41B and 42B, and reference regions 50B are formed of an $SiO_x$ insulator film as in the first embodiment. Working electrodes 200B and reference electrodes 500B are formed of an Au metal film as in the first embodiment. On the other hand, the first regions 31B, 32B, and 33B are formed of, for example, polyimide. Polyimide has a content angle of 60° to 70° with a planar surface. Thus, polyimide has a greater contact angle than $SiO_x$, which has a contact angle less than 30° with a planar surface, but the difference in contact angle therebetween is not greater than or equal to 40°.

In view of this, in the cell retainer 1B, surfaces of the first regions 31B, 32B, and 33B have asperities in the radial direction. Note that the language "having asperities in the radial direction" means that the heights of the surfaces vary periodically depending on the radial position. In the example in FIG. 8, recesses formed in the first regions 31B, 32B, and 33B reach the lower end of the polyimide layer forming the first regions 31B, 32B, and 33B, but the depth of the recesses may be smaller than the thickness of the polyimide layer.

The polyimide serving as the material for the first regions 31B, 32B, and 33B has a greater contact angle with a surface having asperities than with a planar surface. Thus, in the first regions 31B, 32B, and 33B, the contact angle with the surface of polyimide having asperities is greater than 70°. Accordingly, the contact angle in the first regions 31B, 32B, and 33B is greater by 40° or more than the contact angles in the work region 20A and the second regions 41A and 42A, which are formed of $SiO_x$.

As in the example illustrated in FIG. 8, the surfaces of the first regions may have an uneven shape in order to further increase the contact angle in the first regions. By so doing, even if the contact angle with a planer surface of the material for the first regions is not greater enough than the contact angle in the work region and the second regions, the presence of asperities results in a sufficient increase in the contact angle in the first regions.

Note that the surfaces in the first regions may have asperities not only in the radial direction but also in the circumferential direction. The material for the first regions having surfaces of an uneven shape is not limited to polyimide, and may be any material that has a greater contact angle with a planar surface than the materials for the work region and the second regions.

Figure 9:
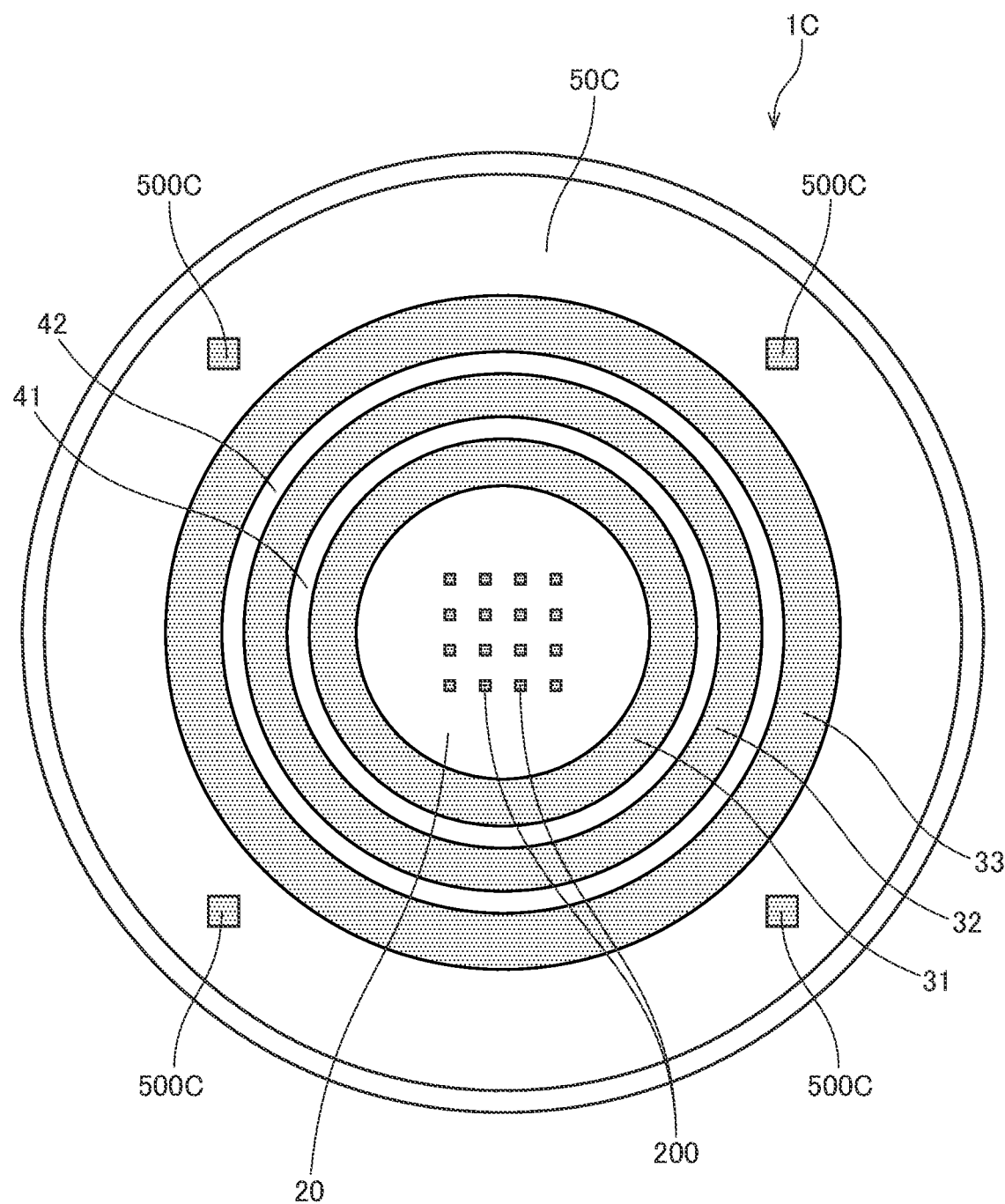
FIG. 9 is a top view of the cell retainer according to another variation.

FIG. 9 is a top view of a cell retainer 1C according to another variation. In FIG. 9, constituent elements that are similar to those of the first embodiment illustrated in FIG. 2 are given the same reference signs. The cell retainer 1C in the example illustrated in FIG. 9 includes four reference electrodes 500C arranged at generally regular intervals in the circumferential direction in a reference region 50C. Each reference electrode 500C has a square shape as viewed from above.

As illustrated in the example in FIG. 9, the number and shape of reference electrodes are not limited to the example described in the first embodiment. Similarly, the number and shape of working electrodes are not limited to the example disclosed in the application of the present invention.

In the embodiment and variations described above, gold (Au) is given as an example of the material for the working electrodes and the reference electrodes, these electrodes may be formed of any other conductive material. Although $SiO_x$ is given as an example of the material for the work region and the reference region, these regions may be formed of any other insulating material. Although gold (Au) and polyimide are given as examples of the material for the first regions, the material may be any other material that has a greater contact angle than the contact angles in the work region and the second regions. Although $SiO_x$ is given as an example of the material for the second regions, the material may be any other material that has a smaller contact angle than the contact angle in the first regions.

The configurations of the embodiment and variations described above may be appropriately combined as long as there are no mutual inconsistencies.

While the invention has been shown and described in detail, the foregoing description is in all aspects illustrative and not restrictive. It is therefore to be understood that numerous modifications and variations can be devised without departing from the scope of the invention.

What is claimed is:

1. A cell retainer comprising:
   a measuring surface on which a cell suspension is dropped, wherein said measuring surface includes:
- a work region in which a plurality of working electrodes are arranged;
- a reference electrode arranged outward of said work region;
- a plurality of first regions provided between said work region and said reference electrode; and
- a second region arranged between two first regions of said plurality of the first regions, the two first regions being adjacent to each other in a radial direction, wherein a contact angle in said plurality of first regions is greater by 40° or more than a contact angle in said work region and a contact angle in said second region, wherein said plurality of first regions each surround said work region in a ring, wherein said plurality of first regions each have a break that is discontinuous in a circumferential direction, wherein wirings extending radially outward from respective ones of said working electrodes are arranged in said break, wherein, in said break, said wirings extending from said working electrodes and said first regions are spaced apart from each other in the circumferential direction, wherein said wirings and said first regions are formed of the same metal film layer on the same plane, and wherein said break is provided such that said wirings do not overlap with said first regions, and said wirings and said first regions are not electrically connected to each other.

2. The cell retainer according to claim 1, wherein said plurality of first regions each have a circular ring shape.

3. The cell retainer according to claim 1, wherein said plurality of first regions are planar in shape, and a contact angle with a planar surface of a material for said plurality of first regions is greater than the contact angle in said work region and the contact angle in said second region.

4. The cell retainer according to claim 1, wherein surfaces of said plurality of first regions have asperities in at least a radial direction, and a material for said plurality of first regions has a greater contact angle with a surface having asperities than with a planar surface.

5. The cell retainer according to claim 1, wherein said working electrodes, said wirings, and surfaces of said first regions are all metal films,
in said break, said metal films of said first regions are interrupted in the circumferential direction, and
said wirings extending from said working electrodes and said metal films of said first regions are arranged spaced apart from each other in the circumferential direction.

6. The cell retainer according to claim 5, wherein said working electrodes, said wirings, and surfaces of said first regions are Au metal films,
a surface of said work region excluding said working electrodes, and a surface of said second region are SiOx film, and
in said break, an upper surface of said wirings is covered with said SiOx film.

* * * * *